United States Patent
Seeboth et al.

(10) Patent No.: US 9,045,432 B2
(45) Date of Patent: *Jun. 2, 2015

(54) NITRILE OXIDE, NITRONE, AND NITRILE IMINE COMPOUNDS

(75) Inventors: Nicolas Seeboth, Clermont-Ferrand (FR); Serguey Ivanov, Orekhovo-Zouevo (RU); Jean-Luc Couturier, Lyons (FR); Manuel Hidalgo, Brignais (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/809,795

(22) PCT Filed: Jul. 12, 2011

(86) PCT No.: PCT/FR2011/051651
§ 371 (c)(1),
(2), (4) Date: Mar. 4, 2013

(87) PCT Pub. No.: WO2012/007684
PCT Pub. Date: Jan. 19, 2012

(65) Prior Publication Data
US 2013/0197237 A1    Aug. 1, 2013

(30) Foreign Application Priority Data
Jul. 13, 2010   (FR) .................................... 10 55717

(51) Int. Cl.
*C07D 233/34*   (2006.01)
*C07D 233/36*   (2006.01)

(52) U.S. Cl.
CPC ............ *C07D 233/34* (2013.01); *C07D 233/36* (2013.01)

(58) Field of Classification Search
CPC .......................... C07D 233/34; C07D 233/36
USPC ............................................ 548/324.1, 323.5
See application file for complete search history.

(56) References Cited

U.S. PATENT DOCUMENTS

| | | |
|---|---|---|
| 5,128,416 A | 7/1992 | Imai |
| 5,329,005 A | 7/1994 | Lawson |
| 5,393,721 A | 2/1995 | Kitamura |
| 7,186,845 B2 | 3/2007 | Fukushima et al. |
| 7,300,970 B2 | 11/2007 | Durel |
| 7,491,767 B2 | 2/2009 | Durel |
| 7,820,771 B2 | 10/2010 | Lapra |
| 7,900,667 B2 | 3/2011 | Vasseur |
| 2004/0010090 A1 | 1/2004 | Chino et al. |
| 2004/0106744 A1 | 6/2004 | Chino |
| 2005/0239639 A1 | 10/2005 | Monteil |
| 2006/0084730 A1 | 4/2006 | Fukushima |
| 2006/0199917 A1 | 9/2006 | Chino |
| 2009/0270558 A1 | 10/2009 | Gandon-pain |
| 2011/0183098 A1 | 7/2011 | Hidalgo et al. |

FOREIGN PATENT DOCUMENTS

| | | |
|---|---|---|
| EP | 0341496 | 11/1989 |
| EP | 0590491 | 4/1994 |
| EP | 0593049 | 4/1994 |
| JP | 2008208163 | 9/2008 |
| WO | 9736724 | 10/1997 |
| WO | 9916600 | 4/1999 |
| WO | 0210269 | 2/2002 |
| WO | 03002648 | 1/2003 |
| WO | 03002649 | 1/2003 |
| WO | 2004035639 | 4/2004 |
| WO | 2006069792 | 7/2006 |
| WO | 2006069793 | 7/2006 |
| WO | WO 2010/031956 | 3/2010 |
| WO | WO 2012/007685 | 1/2012 |

OTHER PUBLICATIONS

Chemical Abstract Service (CAS) STN Registry Database No. 1026443-91-3 [entered STN: Jun. 8, 2008].*
NCBI PubChem Compound CID 263915 [created Mar. 26, 2005].*
Bridgestone Corp. "A denaturation polymer, the rubber composition using it, and a tire." JP 2008/208163A English Machine Translation performed by Google Translation, obtained from the Japan Patent Office AIPN Feb. 4, 2015.*
International Search Report for International Application No. PCT/FR2011/051651 mailed Oct. 25, 2011.
International Search Report for International Application No. PCT/FR2011/051652 mailed Oct. 19, 2011.
International Search Report (PCT/ISA/210) issued on Oct. 5, 2011, by the European Patent Office as the International Searching Authority for International Application No. PCT/EP2011/061799.
International Search Report (PCT/ISA/210) issued on Sep. 29, 2011, by the European Patent Office as the International Searching Authority for International Application No. PCT/EP2011/061801.
M. Galimerti et al., "Elastomeric Compounds with Silica. Lower Hysteresis in the Presence of Functionalised Isoprene Oligomers," Macromolecular Symposia, Mar. 13, 2006, vol. 234, pp. 203-210.

* cited by examiner

*Primary Examiner* — Joseph Kosack
*Assistant Examiner* — Amanda L Aguirre
(74) *Attorney, Agent, or Firm* — RatnerPrestia

(57) ABSTRACT

A compound includes at least one group Q and at least one group A linked together by at least one "spacer" group Sp, in which:
  group Q includes a dipole containing at least one nitrogen atom, preferably a nitrile oxide, nitrone, or nitrile imine function;
  group A contains at least one nitrogen atom, and is preferably an imidazolidinyl, ureyl, bis-ureyl, ureido-pyrimidyl, and triazolyl group; and
  Sp is an atom or a group of atoms forming a link between Q and A, preferably, a linear, branched or cyclic hydrocarbon-based optionally substituted chain, and may contain one or more aromatic radicals and/or heteroatoms. The compound may react with an unsaturated polymer forming a covalent bond with the polymer. The compound is useful for providing good interaction between fillers and polymers by establishing labile, non-covalent bonds between the polymer chains and the filler, thereby limiting processing problems.

6 Claims, No Drawings

NITRILE OXIDE, NITRONE, AND NITRILE IMINE COMPOUNDS

CROSS REFERENCE TO RELATED APPLICATIONS

This application is the U.S. National Phase application of PCT International Application No. PCT/FR2011/051651, filed Jul. 12, 2011, and claims priority to French Patent Application No. 1055717, filed Jul. 13, 2010, the disclosures of which are incorporated by reference in their entirety for all purposes.

This document relates to the subject matter of a joint research agreement between Arkema France, Michelin Recherche et Technique S.A., and Compagnie Generale des Etablissements Michelin.

FIELD OF THE INVENTION

The present invention relates to nitrogenous associative molecules comprising at least one unit rendering them capable of associating with one another or with a filler, via noncovalent bonds, and comprising a function capable of reacting with a polymer containing unsaturations so as to form a covalent bond with said polymer.

In the industrial field, mixtures of polymers with fillers are often used. In order for such mixtures to have good properties, means for improving the dispersion of the fillers within the polymers are constantly being sought. One of the means for achieving this result is the use of coupling agents capable of establishing interactions between the polymer and the filler.

Agents for coupling a polymer with a filler comprising nitrogenous dipoles are described in the documents published under numbers U.S. Pat. No. 7,186,845 B2 and JP2008208163.

These documents describe the modification of polymers comprising diene units with nitrogenous dipolar compounds comprising, in addition, a heterocycle, said heterocycle itself comprising a nitrogen atom, and an oxygen and/or sulfur atom.

More particularly, the compounds described are nitrones bearing oxazoline or thiazoline functions, for instance (–(2-oxazolyl)phenyl-N-methylnitrone).

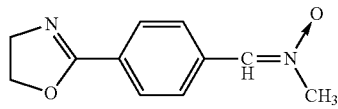

When diene polymers are made to react with such compounds, the polymers resulting therefrom will bear the oxazoline or thiazoline rings.

These rings present on the polymer are capable of reacting, in turn, with surface functions of the fillers (such as carbon black or silica) with which the polymers are mixed. This reaction results in the forming of covalent bonds between the polymer modified with the coupling agent and the filler owing to the opening of the oxazoline or thiazoline ring. Indeed, as it is described in document U.S. Pat. No. 7,186,845 B2, the oxazoline and/or thiazoline rings are capable of opening in the presence of a nucleophile which may, for example, be present at the surface of the filler.

The forming of such covalent bonds has, on the other hand, drawbacks during the preparation of mixtures comprising these polymers, modified with coupling agents, with fillers. In particular, the existence of these covalent bonds formed early on, between the polymer and the fillers, makes these mixtures very viscous in the non-crosslinked state, which makes all operations prior to the crosslinking (vulcanization) of rubber-based formulations difficult, in particular the preparation of mixtures of constituents, and the forming thereof; these drawbacks have a strong impact on industrial productivity. It is therefore desirable to propose novel molecules which do not have the above drawbacks, i.e. molecules which are capable, after reaction with a polymer and mixing with a filler, of not forming covalent bonds with the filler and therefore of not causing too great an increase in the viscosity of the mixture.

SUMMARY OF THE INVENTION

A subject of the invention is a compound comprising at least one group Q and at least one group A linked together by at least and preferably one "spacer" group Sp, in which:

Q comprises a dipole containing at least and preferably one nitrogen atom,

A comprises an associative group comprising at least one nitrogen atom,

Sp is an atom or a group of atoms forming a link between Q and A.

A polymer grafted with a compound as defined above is mixed with fillers, as said compound establishes only labile bonds with the fillers, which makes it possible to provide good polymer-filler interaction, beneficial for the final properties of the polymer, but without the drawbacks that too strong a polymer-filler interaction could cause.

The compounds which are subjects of the invention provide good interaction with the fillers by establishing labile bonds between the polymer chains and the filler, and thus limit the processing problems.

DETAILED DESCRIPTION

The term "dipole" is intended to mean a function capable of forming a 1,3 dipolar addition on an unsaturated carbon-carbon bond.

The term "associative group" is intended to mean groups capable of associating with one another via hydrogen, ionic and/or hydrophobic bonds. They are, according to one preferred embodiment of the invention, groups capable of associating via hydrogen bonds.

When the associative groups are capable of associating via hydrogen bonds, each associative group comprises at least one donor "site" and one acceptor site with respect to the hydrogen bond such that two identical associative groups are self-complementary and can associate with one another by forming at least two hydrogen bonds.

The associative groups according to the invention are also capable of associating via hydrogen, ionic and/or hydrophobic bonds with functions present on the fillers.

The compounds according to the invention comprising a group Q, a "spacer" group and an associative group can, for example, be represented by formula (Ia) below:

A-Sp-Q    (Ia).

The compounds according to the invention comprising a group Q, a "spacer" group and two associative groups can, for example, be represented by formula (Ib) below:

(Ib)

Similarly, the compounds according to the invention comprising two groups Q, a "spacer" group and an associative group can, for example, be represented by formula (Ic) below:

(Ic)

According to the same principle, the compounds according to the invention comprising two groups Q, a "spacer" group and two associative groups can, for example, be represented by formula (Id) below:

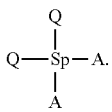
(Id)

Preferably, the associative group is chosen from an imidazolidinyl, ureyl, bis-ureyl, ureido-pyrimidyl, and triazolyl group.

Preferably, the group A corresponds to one of the formulae (II) to (VI) below:

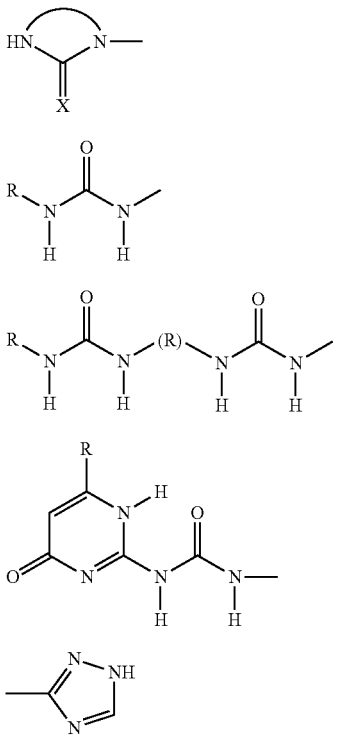

wherein:
R denotes a hydrocarbon-based group which can optionally contain heteroatoms,
X denotes an oxygen or sulfur atom, preferably an oxygen atom.

Preferably, the group A comprises a dinitrogenous or trinitrogenous heterocycle, containing 5 or 6 atoms, which is preferably dinitrogenous, and which comprises at least one carbonyl function.

In at least one embodiment, the group A comprises an imidazolidinyl group of the formula (II).

The group Q is capable of bonding to a polymer chain comprising at least one unsaturation by covalent bonding (grafting). Preferably, the group Q comprises a nitrile oxide, nitrone or nitrile imine function which can bond to a polymer bearing unsaturations, via a cycloaddition of [3+2] type.

Preferably, the group Q is a group of formula (VII), (VIII) or (IX) below

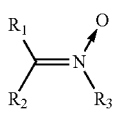
(VII)

(VIII)

(IX)

in which R1 to R6 are chosen independently from a spacer group Sp, a hydrogen atom, a linear or branched $C_1$-$C_{20}$ alkyl group, a linear or branched $C_3$-$C_{20}$ cycloalkyl group, a linear or branched $C_6$-$C_{20}$ aryl group, and a group of formula (X)

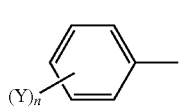
(X)

in which n represents 1, 2, 3, 4 or 5 and each Y independently represents a spacer group Sp, an alkyl group or a halogen.

The "spacer" group Sp makes it possible to link at least one group Q and/or at least one associative group A, and thus may be of any type known per se. However, the "spacer" group must interfere little or not at all with the groups Q and associative groups of the compound according to the invention.

Said "spacer" group is therefore considered to be a group that is inert with respect to the group Q and the associative group. The expression ""spacer" which is inert with respect to the group Q" is intended to mean: which does not have alkenyl or alkynyl functions capable of reacting with this group. The expression ""spacer" which is inert with respect to the associative group" is intended to mean: which does not comprise associative functions as defined according to the invention.

The "spacer" group is preferably a linear, branched or cyclic hydrocarbon-based chain, and can contain one or more aromatic radicals, and/or one or more heteroatoms. Said chain can optionally be substituted, provided that the substituents are inert with respect to the groups Q and associative groups.

According to one preferred embodiment, the "spacer" group is a linear or branched $C_1$-$C_{24}$, preferably $C_1$-$C_{10}$, alkyl chain, such as a linear $C_1$-$C_6$ alkyl chain, optionally interrupted with one or more nitrogen or oxygen atoms.

Preferably, the group Q is a group of formula (XI):

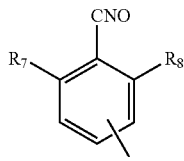
(XI)

in which R7 and R8 independently represent a $C_1$-$C_5$ alkyl group or a halogen, and preferably R7 and R8 independently represent a methyl group or a chlorine atom, and the group A is a group of formula (XII):

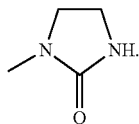
(XII)

Preferably, the compound which is the subject of the invention is chosen from the compounds of formulae (XIII) to (XXI) below:

(XIII)

(XIV)

(XV)

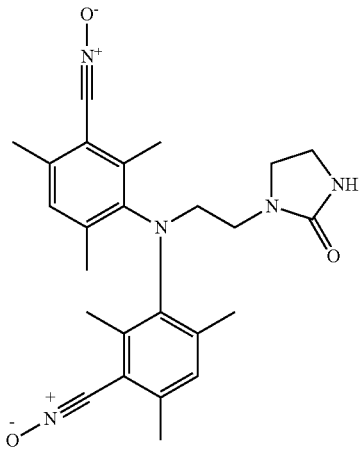
(XVI)

(XVII)

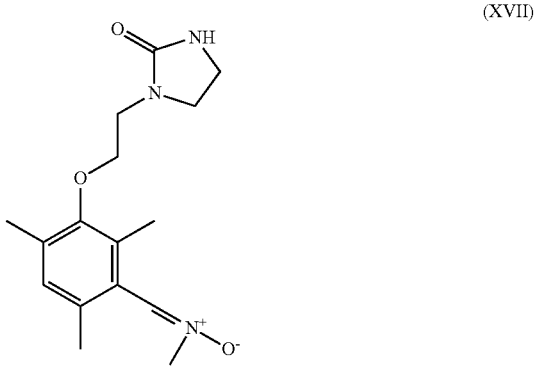
(XVIII)

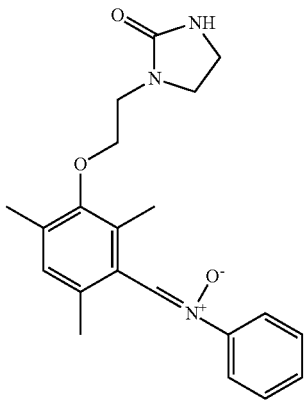
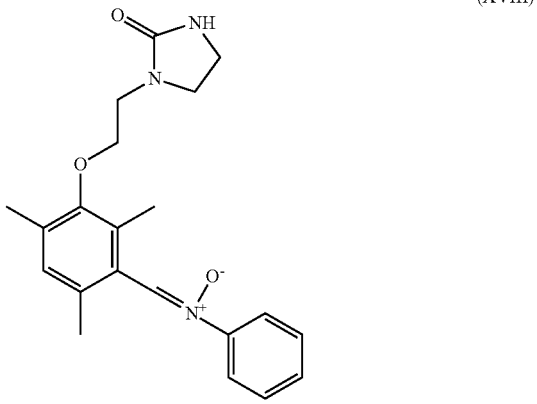
(XIX)

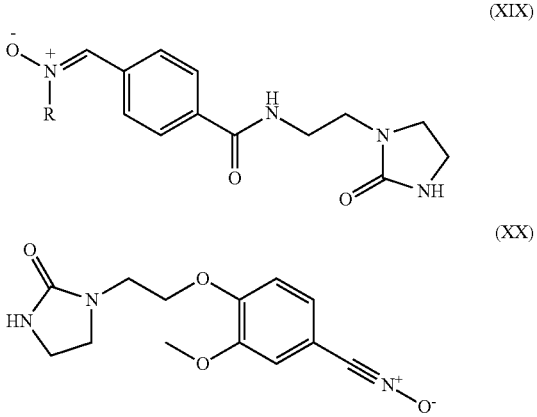
(XX)

(XXI)

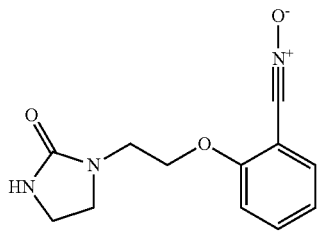

According to another embodiment of the invention, the compound intended for grafting the polymer in accordance with the invention is chosen from the compound of formulae (XXII) to (XXIII) below:

(XXII)

(XXIII)

in which R is chosen from a spacer group Sp, a hydrogen atom, a linear or branched $C_1$-$C_{20}$ alkyl group, a linear or branched $C_3$-$C_{20}$ cycloalkyl group, a linear or branched $C_6$-$C_{20}$ aryl group, and a group of formula (X)

(X)

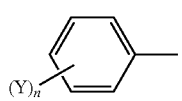

in which n represents 1, 2, 3, 4 or 5 and each Y independently represents a spacer group Sp, an alkyl group or a halide.

The invention is also illustrated by the following nonlimiting examples.

EXEMPLARY EMBODIMENTS

The structural analysis and also the determination of the molar purities of the synthetic molecules were carried out by NMR analysis. The spectra were acquired on a Bruker Avance 500 MHz spectrometer equipped with a BBIz-grad 5 mm "broad-band" probe. The quantitative $^1$H NMR experiment used a simple 30° pulse sequence and a repetition delay of 3 seconds between each of the 64 acquisitions. The samples were solubilized in deuterated dimethyl sulfoxide (DMSO). This solvent was also used for the lock signal. The calibration was carried out on the proton signal for the deuterated DMSO at 2.44 ppm relative to a TMS reference at 0 ppm. The $^1$H NMR spectrum coupled with the 2D HSQC 1H/13C and HMBC 1H/13C experiments enabled the structural determination of the molecules (cf. assignment tables). The molar quantifications were carried out on the basis of the quantitative 1D $^1$H NMR spectrum.

The infrared measurement made it possible to validate the presence of the nitrile oxide group borne by an aromatic. The spectra were acquired on a Vertex 70 Fourier transform spectrometer fitted with a DTGS detector. The spectra were acquired in 32 scans between 4000 cm$^{-1}$ and 400 cm$^{-1}$ with a resolution of 2 cm$^{-1}$. The samples were prepared in the form of KBr pellets. The nitrile oxide function borne by the aromatic was characterized by a band at 2295 cm$^{-1}$.

The mass spectrometry analysis was carried out by direct injection in electrospray ionization mode (DI/ESI). The analyses were carried out on a Bruker HCT spectrometer (flow rate 600 μL/min, nebulizing gas pressure 10 psi, nebulizing gas flow rate 4 L/min).

Example 1

Preparation of 1-(2-(3'-nitriloxymesityl-1'-oxy)ethyl) imidazolidin-2-one

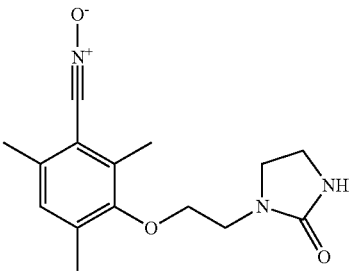 [SMILES: Cc1cc(C)c(OCCN2CCNC2=O)c(C)c1C#[N+][O-]]

This compound can be prepared from hydroxyethyl-imidazolidone mesitol according to the following synthesis scheme.

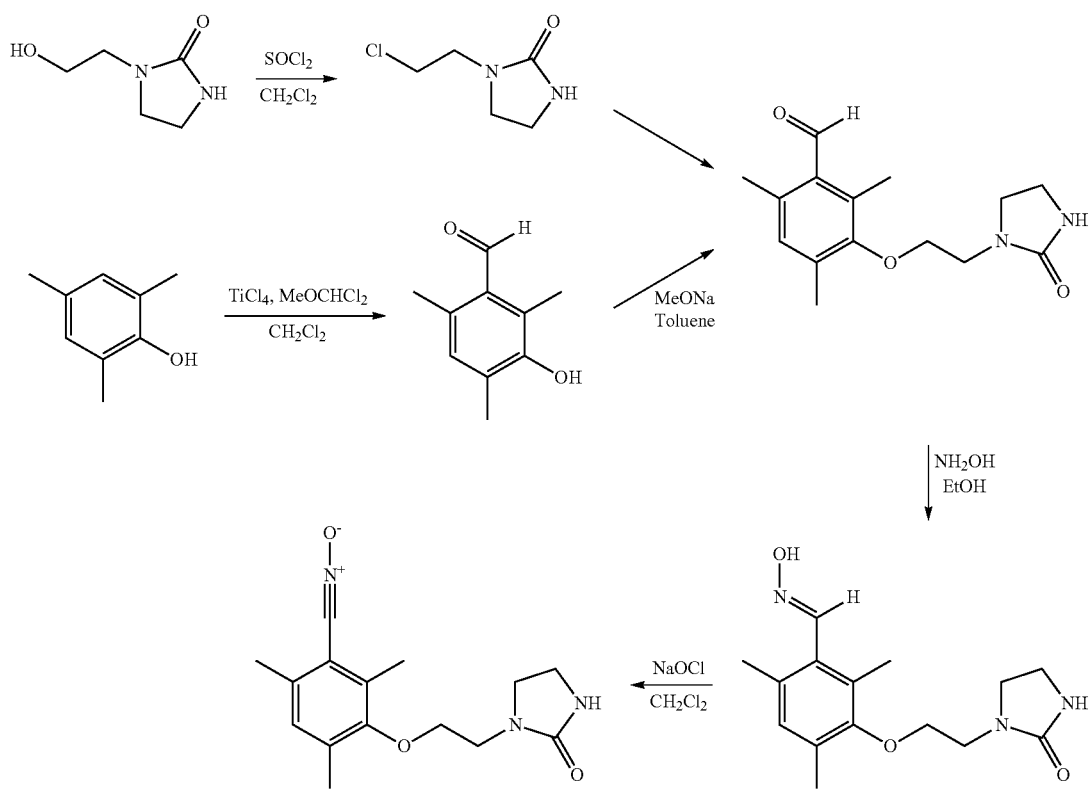

a) Preparation of
3-hydroxy-2,4,6-trimethylbenzaldehyde

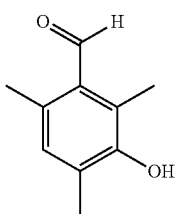

This compound can be obtained according to a procedure described in the following article: Yakubov, A. P.; Tsyganov, D. V.; Belen'kii, L. I.; Krayushkin, M. M.; *Bulletin of the Academy of Sciences of the USSR, Division of Chemical Science (English Translation)*; vol. 40; nb. 7.2; (1991); p. 1427-1432; *Izvestiya Akademii Nauk SSSR, Seriya Khimicheskaya*; nb. 7; (1991); p. 1609-1615.

b) Preparation of
1-(2-chloroethyl)imidazolidin-2-one

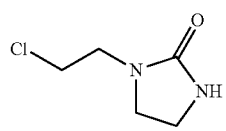

This product is described in the article Nagarajan K., Arya V. P., Shah R. K.; *Indian Journal of Chemistry, Section B: Organic Chemistry Including Medicinal Chemistry;* 21; 10; 1982; 928-940.

Thionyl chloride (34 ml, 0.47 mol) was added, dropwise, at ambient temperature, over a period of 35 minutes, to a solution of 1-(2-hydroxyethyl)imidazolidin-2-one (50.0 g, 0.39 mol) in dichloromethane (250 ml). At the end of the addition, the temperature of the reaction medium was 35° C. The reaction medium was maintained at a temperature of 35-40° C. for 2.5 hours. After evaporation under reduced pressure ($T_{bath}$ 35° C., 15-17 mbar), the crude product was obtained (67 g). This crude was crystallized from a mixture of acetone and petroleum ether (35 g for 950 ml of acetone and 820 ml of petroleum ether at −24° C. for 10 to 15 hours). The crystals were filtered off, washed with petroleum ether (twice with 40 ml), then dried for 10 to 15 hours under atmospheric pressure at ambient temperature.

A white solid (33.3 g, yield 66%) with a melting point of 93° C. was obtained.

The molar purity was greater than 97% ($^1$H NMR).

A $^1$H and $^{13}$C NMR characterization is provided in the following table 1.

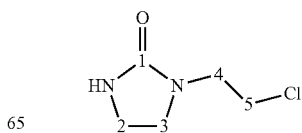

TABLE 1

| Atom | δ $^1$H (ppm) + mult. | δ $^{13}$C (ppm) |
|---|---|---|
| 1 | — | 162.1 |
| 2 | 3.17 (t) | 37.5 |
| 3 | 3.33 (t) | 44.7 |
| 4 | 3.29 (t) | 45.0 |
| 5 | 3.62 (t) | 42.4 |

Solvent used: DMSO—Calibration on the signal of the DMSO at 2.44 ppm in $^1$H, 39.5 ppm in $^{13}$C.

c) Preparation of 2,4,6-trimethyl-3-(2-(2-oxoimidazolidin-1-yl)ethoxy)benzaldehyde

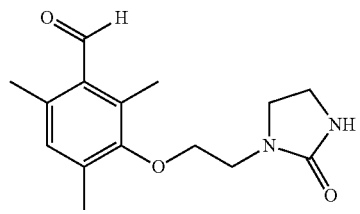 [SMILES: Cc1cc(C)c(OCCN2CCNC2=O)c(C)c1C=O]

3-Hydroxy-2,4,6-trimethylbenzaldehyde (11.90 g, 0.073 mol) in anhydrous toluene (300 ml) was added dropwise to a solution of sodium (1.63 g, 0.071 mol) in methanol (60 ml). The mixture was brought to reflux and then the methanol was distilled off (volume of azeotropic mixture collected 80-90 ml). After a return to 80-90° C., (2-chloroethyl)imidazolidin-2-one (10.45 g, 0.070 mol) was added in one step to the reaction medium. After refluxing for 7 hours, the solvents were evaporated off under reduced pressure (T$_{bath}$ 50° C., 25 mbar). Dichloromethane (150 ml) and water (30 ml) were added to the mixture obtained. The organic phase was then washed twice with water (20 ml). After drying over Na$_2$SO$_4$, the dichloromethane was evaporated off under reduced pressure (T$_{bath}$ 35° C., 33 mbar). Petroleum ether (3 times 50 ml) and water (50 ml) were added to the mixture obtained (24 g) and the precipitate obtained was filtered off and washed on the filter with water (15 ml) and petroleum ether (twice with 15 ml).

The product obtained was repurified by washing the product in solution in dichloromethane (80 ml) with a solution of NaOH at 4% in water (3 times with 60 ml). After evaporation of the solvents under reduced pressure, the product was precipitated from petroleum ether. The precipitate was filtered off and dried for 15 to 20 hours under atmospheric pressure at ambient temperature.

A white solid (8.55 g, yield 44%) with a melting point of 139° C. was obtained.

The molar purity was greater than 94% ($^1$H NMR).

A $^1$H and $^{13}$C NMR characterization is provided in the following table 2.

TABLE 2

| Atom | δ $^1$H (ppm) + mult. | δ $^{13}$C (ppm) |
|---|---|---|
| 1 | — | 163.1 |
| 2 | ~4.74 (s) | — |
| 3 | 3.40 (t) | 38.1 |
| 4 | 3.65 (t) | 46.8 |
| 5 | 3.52 (t) | 43.9 |
| 6 | 3.79 (t) | 71.3 |
| 7 | — | 153.9 |
| 8 | — | * |
| 9 | 2.23/2.46 (s) | 16.5/19.8 |
| 10 | 6.84 | 131.7 |
| 11 | — | * |
| 12 | 2.23/2.46 (s) | 16.5/19.8 |
| 13 | — | * |
| 14 | ~10.46 (s) | 193.0 |
| 15 | — | * |
| 16 | 2.46 (s) | 12.1 |

* 131.4/133.5/136.6/136.7 ppm: The aromatic ring $^{13}$C chemical shifts are not assigned.

Solvent used: CDCl$_3$—Calibration on the signal of chloroform at 7.2 ppm in $^1$H, 77 ppm in $^{13}$C.

d) Preparation of 2,4,6-trimethyl-3-(2-(2-oxoimidazolidin-1-yl)ethoxy)benzaldehyde oxime

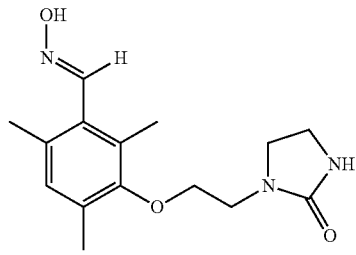

A solution of aqueous hydroxylamine (2.83 g, 0.043 mol, 50% in water) in ethanol (10 ml) was added to a solution of 2,4,6-trimethyl-3-(2-(2-oxoimidazolidin-1-yl)ethoxy)benzaldehyde (7.90 g, 0.029 mol) in ethanol (70 ml) maintained at a temperature of 45° C. The reaction medium was then stirred for 2.5 hours at a temperature between 50 and 55° C. The solvent was evaporated off under reduced pressure (T$_{bath}$ 37° C., 35 mbar). Petroleum ether (80 ml) was added to the crude obtained. The precipitate obtained was filtered off, washed with petroleum ether (twice with 20 ml) and dried for 15 to 20 hours under atmospheric pressure at ambient temperature.

A white solid (7.82 g, yield 94%) with a melting point of 165° C. was obtained.

The molar purity was greater than 84% (the remaining 16% comprised in particular 7 mol % of EtOH) according to the $^1$H NMR.

A $^1$H and $^{13}$C NMR characterization is provided in the following table 3.

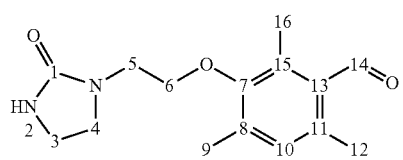

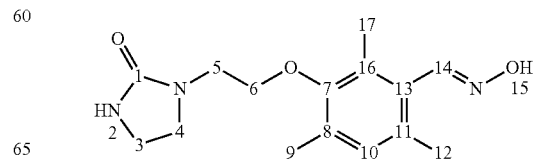

TABLE 3

| Atom | δ ¹H (ppm) + mult. | δ ¹³C (ppm) |
|---|---|---|
| 1 | — | 162.0 |
| 2 | ~6.30 (s) | — |
| 3 | 3.19 (t) | 37.1 |
| 4 | 3.44 (t) | 45.5 |
| 5 | 3.34 (t) | 43.2 |
| 6 | 3.69 (t) | 70.3 |
| 7 | — | 153.5 |
| 8 | — | * |
| 9 | 2.14 (s) | 15.4 |
| 10 | — | 130.5 |
| 11 | — | * |
| 12 | 2.18 (s) | 19.9 |
| 13 | — | * |
| 14 | ~8.20 (s) | 147.4 |
| 15 | ~11.10 (s) | — |
| 16 | — | * |
| 17 | 2.17 (s) | 12.9 |

* 129.3/129.5/131.9 ppm: The aromatic ring ¹³C chemical shifts are not assigned, three signals are detected (probably two carbons under one and the same signal).

Solvent used: DMSO—Calibration on the signal of DMSO at 2.44 ppm in ¹H, 39.5 ppm in ¹³C.

e) Preparation of 2,4,6-trimethyl-3-(2-(2-oxoimidazolidin-1-yl)ethoxy)nitrile oxide, Compound According to the Invention

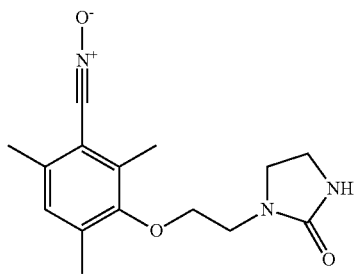 [SMILES: Cc1cc(C)c(OCCN2CCNC2=O)c(C)c1C#[N+][O-]]

An aqueous solution of NaOCl (4% of active chlorine, 52 ml) was added, dropwise, over a period of 5-7 minutes, to a solution of oxime previously prepared (6.00 g, 0.021 mol) in dichloromethane (250 ml), at a temperature of 2° C. The temperature of the reaction medium was maintained between 0 and −4° C. The reaction medium was then stirred for 3 hours at a temperature between 0 and 5° C. The organic phase was then separated. The aqueous phase was extracted with dichloromethane (twice with 15 ml). The organic phases were combined and then washed with water (twice with 20 ml, and dried with $Na_2SO_4$. The solvent volume was reduced by evaporation under reduced pressure ($T_{bath}$ 22° C., 220 mbar) to 50-60 ml. Petroleum ether (75 ml) was then added and the solution was placed at −18° C. for 10-15 hours. The precipitate obtained was filtered off and washed with an ethyl acetate/petroleum ether (1/2) mixture (10 ml) and, finally, dried for 10-15 hours under atmospheric pressure at ambient temperature.

A white solid (4.70 g, yield 79%) with a melting point of 156° C. was obtained.

The molar purity was greater than 85% (¹H NMR).

A ¹H and ¹³C NMR characterization is provided in the following table 4.

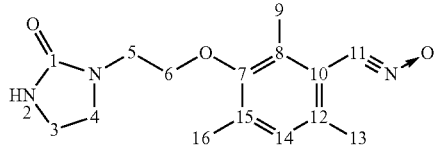

TABLE 4

| Atom | δ ¹H (ppm) + mult. | δ ¹³C (ppm) |
|---|---|---|
| 1 | — | Not detected, not assigned |
| 2 | ~4.59 (s) | — |
| 3 | 3.41 (t) | 38.3 |
| 4 | 3.64 (t) | 47.0 |
| 5 | 3.51 (t) | 44.1 |
| 6 | 3.79 (t) | 71.5 |
| 7 | — | 153.6 |
| 8 | — | 134.4/137.3* |
| 9 | 2.32 (s) | 14.8 |
| 10 | — | 112.8 |
| 11 | — | Not detected, not assigned |
| 12 | — | 134.4/137.3* |
| 13 | 2.31 (s) | 20.2 |
| 14 | 6.85 (s) | 130.3 |
| 15 | — | 134.4/137.3* |
| 16 | 2.20 (s) | 16.4 |

*The aromatic carbons 8, 12 and 15 are not assigned. Two signals are observed in ¹³C NMR, there are probably two carbons which leave under the same signal.

The —C≡N→O function exhibits a characteristic IR band at 2295 $cm^{-1}$.

Solvent used: $CDCl_3$—Calibration on the signal of chloroform at 7.2 ppm in ¹H, 77 ppm in ¹³C.

Example 2

Preparation of 2-[2-(2-oxoimidazolidin-1-yl)ethoxy]benzonitrile oxide

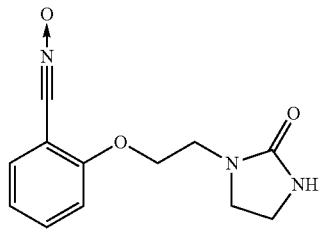 [SMILES: O=C1NCCN1CCOc1ccccc1C#[N+][O-]]

This compound can be prepared from salicylic aldehyde and 2-chloroethylimidazolidone according to the following synthesis scheme:

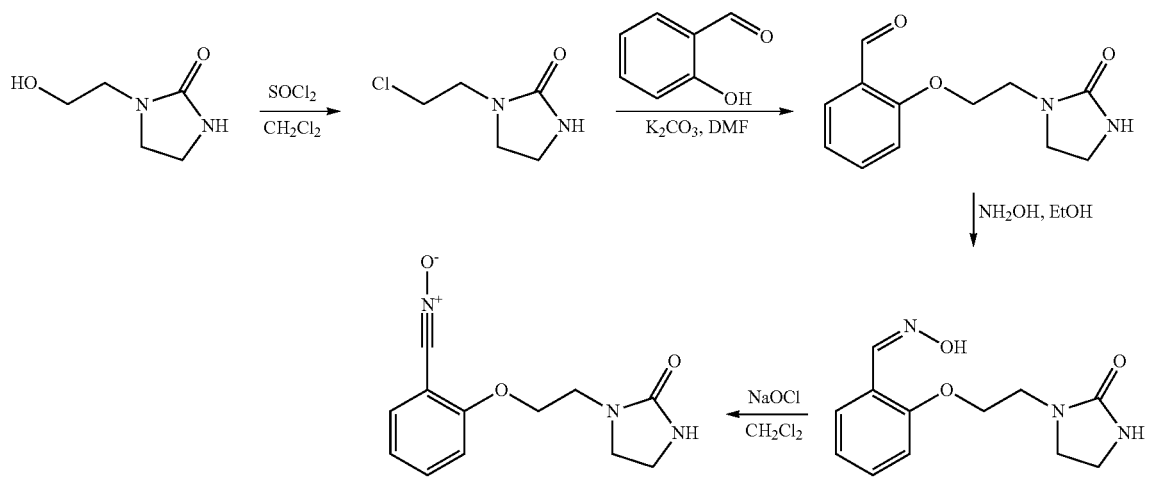

a) The Preparation of 1-(2-chloroethyl)imidazolidin-2-one is Described in Example 1

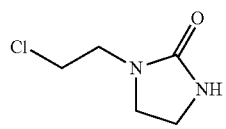

b) Preparation of 2-[2-(2-oxoimidazolidin-1-yl)ethoxy]benzaldehyde

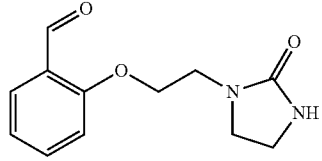 [SMILES: O=Cc1ccccc1OCCN1CCNC1=O]

K$_2$CO$_3$ (87.1 g, 0.631 mol) was added to a solution of salicylic aldehyde (22.0 g, 0.180 mol) in DMF (100 ml). The mixture is stirred at 52° C. After 10 minutes at this temperature, 1-(2-chloroethyl)imidazolidin-2-one (40.0 g, 0.270 mol, purity >90%) was added portionwise. The temperature of the mixture was brought to 90° C. (T$_{bath}$) over the course of one hour and this temperature was maintained for 5 hours. After return to ambient temperature, the mixture was diluted with water (1.3 l) and the product was extracted with CH$_2$Cl$_2$ (500 ml, 5 times 100 ml). The organic phases were combined, then washed with water (twice with 50 ml) and evaporated until a reaction crude of 70-80 g is obtained (dense suspension) (T$_{bath}$=40° C.). The reaction crude was taken up in Et$_2$O (120 ml) and the suspension was stirred at ambient temperature for 20 minutes. The precipitate obtained was filtered off and washed with a mixture of DMF/Et$_2$O/H$_2$O (5 ml/20 ml/15 ml) then with Et$_2$O (twice with 10 ml). The solid obtained was dried at ambient temperature.

A solid (30.6 g, yield 73%) with a melting point of 150° C. was obtained. The molar purity was greater than 84% ($^1$H NMR).

The 2-[2-(2-oxoimidazolidin-1-yl)ethoxy]benzaldehyde obtained was directly used in the next step without further purification.

$^1$H and $^{13}$C NMR Characterization

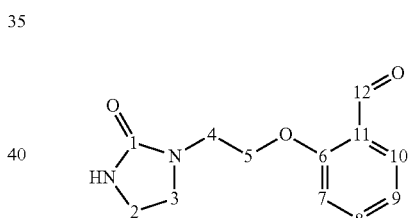

TABLE 5

| Atom | δ $^1$H (ppm) | δ $^{13}$C (ppm) |
|---|---|---|
| 1 | — | 164.9 |
| 2 | 3.15 | 37.3 |
| 3 | 3.39 | 44.9 |
| 4 | 3.44 | 42.1 |
| 5 | 4.16 | 66.5 |
| 6 | — | 160.5 |
| 7 | 7.17 | 113.2 |
| 8 | 7.59 | 136.2 |
| 9 | 7.02 | 120.5 |
| 10 | 7.63 | 127.3 |
| 11 | — | 124.0 |
| 12 | 10.31 | 189.1 |

Solvent used: DMSO—Calibration on the signal of DMSO at 2.44 ppm in $^1$H, 39.5 ppm in $^{13}$C.

c) Preparation of 2-[2-(2-oxoimidazolidin-1-yl)ethoxy]benzaldehyde oxime

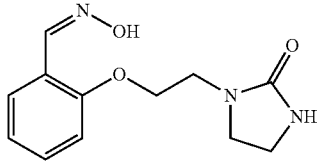 [SMILES: O=C1NCCN1CCOc1ccccc1/C=N\O]

A solution of 2-[2-(2-oxoimidazolidin-1-yl)ethoxy]benzaldehyde (10.0 g, 0.043 mol) in EtOH (100 ml) was brought to 50° C. At this temperature, a solution of hydroxylamine (4.5 g, 0.068 mol, 50% in water, Aldrich) in EtOH (10 ml) was added. The reaction medium was then stirred for 6 hours at a temperature between 50° C. and 70° C. The reaction medium was evaporated under reduced pressure ($T_{bath}$ 45° C., 65-70 mbar) until a suspension was obtained. The reaction crude was then taken up in water (5 ml). The solution obtained was cooled to 5° C. and maintained at this temperature for 15 hours. The precipitate obtained was filtered off and washed on the filter with an EtOH/water (2 ml/2 ml) mixture, then with an EtOH/petroleum ether (1 ml/4 ml) mixture, then with petroleum ether (2×10 ml). The solid was then dried under atmospheric pressure at ambient temperature.

A white solid (9.25 g, yield 87%) with a melting point of 88° C. was obtained.

The molar purity was greater than 99% ($^1$H NMR).

$^1$H and $^{13}$C NMR Characterization

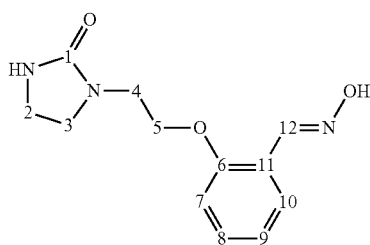

Solvent used: DMSO=Calibration on the signal of DMSO at 2.44 ppm in $^1$H, 39.5 ppm in $^{13}$C.

d) Preparation of 2-[2-(2-oxoimidazolidin-1-yl)ethoxy]benzonitrile oxide

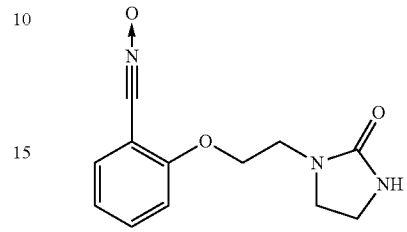

An aqueous solution of NaOCl in water (157 ml, Aldrich, >4% of active chlorine) was added dropwise, over a period of 10 minutes, to a suspension of 2-[2-(2-oxo-imidazolidin-1-yl)ethoxy]benzaldehyde oxime (20.2 g, 0.081 mol) in CH$_2$Cl$_2$ (400 ml) at −1° C. The reaction medium was then stirred for 20 minutes. The aqueous and organic phases were separated and the aqueous phase was extracted with CH$_2$Cl$_2$ (twice at 75 ml). The combined organic phases were washed with water (3 times 10 ml) and dried over Na$_2$SO$_4$. The phases were concentrated to 100 ml under reduced pressure at ambient pressure. 50 ml of petroleum ether were added. The solution was cooled to −18° C. (3 hours). The precipitate was filtered off, washed with CH$_2$Cl$_2$/petroleum ether (5 ml/10 ml; then 5 ml/20 ml; then 0 ml/20 ml), then dried under atmospheric pressure at ambient temperature.

A solid (11.32 g, yield 57%) with a melting point of 109-110° C. with decomposition of the product was obtained.

The molar purity was greater than 94% ($^1$H NMR).

$^1$H and $^{13}$C NMR Characterization

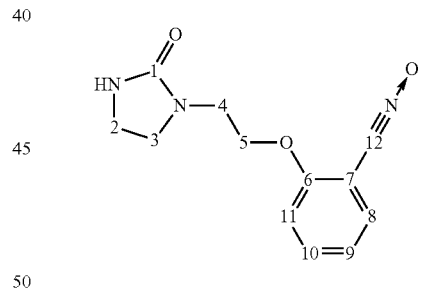

TABLE 6

| Atom | δ $^1$H (ppm) | δ $^{13}$C (ppm) |
| --- | --- | --- |
| 1 | — | 162.0 |
| 2 | 3.17 | 37.4 |
| 3 | 3.37 | 45.4 |
| 4 | 3.39 | 42.6 |
| 5 | 4.03 | 66.6 |
| 6 | — | 155.8 |
| 7 | 7.01 | 113.0 |
| 8 | 7.28 | 130.7 |
| 9 | 6.89 | 121.2 |
| 10 | 7.61 | 125.2 |
| 11 | — | 120.9 |
| 12 | 8.25 | 143.3 |

TABLE 7

| Atom | δ $^1$H (ppm) | δ $^{13}$C (ppm) |
| --- | --- | --- |
| 1 | — | 162.0 |
| 2 | 3.18 | 37.5 |
| 3 | 3.45 | 45.8 |
| 4 | 3.39 | 42.5 |
| 5 | 4.14 | 67.9 |
| 6 | — | 159.9 |
| 7 | — | 101.6 |
| 8 | 7.60 | 133.4 |
| 9 | 7.00 | 121.2 |
| 10 | 7.48 | 132.9 |
| 11 | 7.16 | 112.6 |
| 12 | — | Not observed |
| NH | ~6.34 | — |

Solvent used: DMSO—Calibration on the signal of DMSO at 2.44 ppm in $^1$H, 39.5 ppm in $^{13}$C.
Infrared Characterization (KBr Pellet)
ν (cm$^{-1}$): 2295 (function Ar—C≡N→O)
Mass Spectrometry Characterization
$C_{12}H_{13}N_3O_3$, Mw=247.25 g/mol
The samples were analyzed by direct introduction into the mass spectrometer, using the electrospray ionization mode (DI/ESI).
Preparation of the Sample
20 mg of the sample are dissolved in 2 ml of acetonitrile.
m/z: 270 ([[M+Na]$^+$), 517 ([2M+Na]$^+$)

Example 3

Preparation of 3-methoxy-4-[(2-(2-oxoimidazolidin-1-yl)ethoxy]benzonitrile oxide This compound can be prepared from vanillin and 2-chloroethylimidazolidone according to the following synthesis scheme:

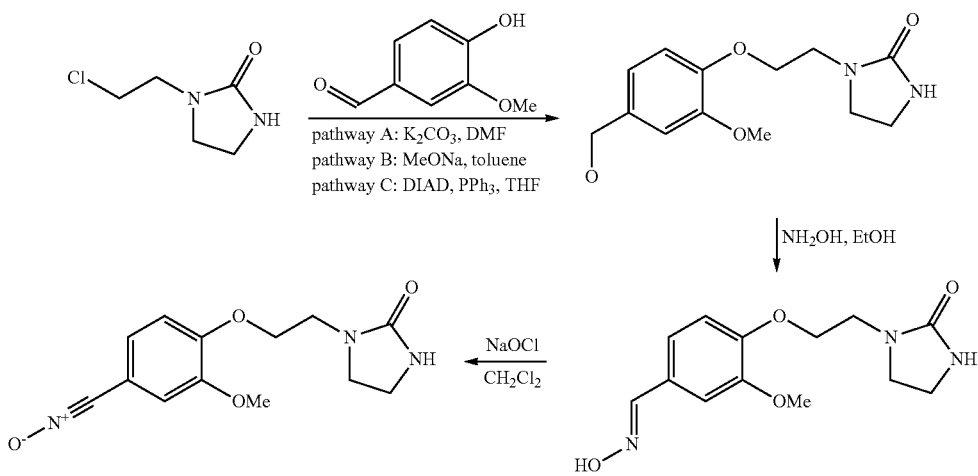

a) Preparation of 3-methoxy-4-[2-(2-oxoimidazolidin-1-yl)ethoxy]benzaldehyde

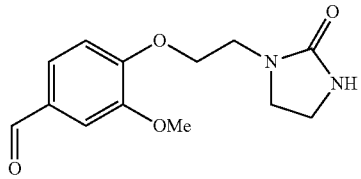 [SMILES: COc1cc(C=O)ccc1OCCN1CCNC1=O]

Pathway A

A suspension of vanillin (30.0 g, 0.197 mol) and of $K_2CO_3$ (95.4 g, 0.690 mol) in DMF (200 ml) was brought to 50° C. for 15 minutes. 1-(2-Chloroethyl)imidazolidin-2-one (44.0 g, 0.296 mol, purity >90%) in DMF (30 ml) was added portionwise to this suspension. The reaction medium was heated to 90° C. ($T_{bath}$) and this temperature was maintained for approximately 4 hours. The reaction medium was brought back to ambient temperature and then water (1.25 l) was added. The product was extracted with $CH_2Cl_2$ (400 ml, 4 times 100 ml). The combined organic phases were washed with water (60 ml) and concentrated under reduced pressure, (14 mbar, 40° C.). The reaction crude was diluted with $Et_2O$ (100 ml) and the suspension was stirred at ambient temperature for 15-20 minutes. The precipitate obtained was filtered off, washed with $Et_2O$ (3 times with 15 ml) and dried at ambient temperature.

A solid (31.2 g, yield 60%) with a melting point of 130° C. was obtained.

The molar purity was greater than 92% ($^1$H NMR).

Pathway B

Vanillin (10.0 g, 0.066 mol) in anhydrous toluene (250 ml) was added to a solution of sodium (1.51 g, 0.066 mol) in $CH_3OH$ (60 ml). The reaction medium, under an inert atmosphere, was brought to reflux and then the residual methanol was distilled off. After a return to 80-90° C., a suspension of 1-(2-chloroethyl)imidazolidin-2-one (9.28 g, 0.064 mol, purity>95%) in toluene (50 ml) was added to the reaction medium in one step. After reaction for 25 hours, the reaction medium was concentrated under reduced pressure ($T_{bath}$ 50° C., 30 mbar). The reaction crude was taken up in $CH_2Cl_2$ (150 ml). The unreacted vanillin was removed by extraction with an aqueous 7% NaOH solution (5 times with 30 ml). The combined organic phases were washed with water (4 times 50 ml), dried under $Na_2SO_4$ and evaporated under reduced pressure ($T_{bath}$ 27° C., 20 mbar). The reaction crude (4.81 g) was diluted with a mixture of petroleum ether and EtOAc, and the precipitate obtained was filtered off.

A solid (0.91 g, yield 6%) with a melting point of 127° C. was obtained.

The molar purity was greater than 81% ($^1$H NMR).

Pathway C

The procedure of the Mitsunobu reaction is, for example, described in the following references: Mitsunobu, O.; Yamada, Y. *Bull. Chem. Soc. Japan* 1967, 40, 2380-2382, *The Use of Diethyl Azodicarboxylate and Triphenylphosphine in Synthesis and Transformation of Natural Products* Mitsunobu, O. *Synthesis* 1981, 1-28, patent EP1149092 B1, 2003.

A solution of diisopropyl azodicarboxylate (10.1 g, 0.050 mol, Aldrich) in anhydrous THF (150 ml) was added dropwise, over a period of 20 minutes, to a solution of vanillin (5.02 g, 0.033 mol), anhydrous 1-(2-hydroxy-ethyl)imidazolidin-2-one (6.38 g, 0.049 mol, Aldrich) and $PPh_3$ (13.1 g, 0.050 mol) in anhydrous THF (300 ml) at 2° C. The reaction medium was stirred for 14 hours at ambient temperature and was then diluted with water (150 ml). The reaction medium was concentrated under reduced pressure (45 mbar, $T_{bath}$ 28° C.). The aqueous phase was extracted with EtOAc (3 times with 200 ml). The combined organic phases were washed with a saturated aqueous solution of NaCl and were then concentrated under reduced pressure so as to obtain a solution of 150 ml. The reaction crude in solution was purified by column chromatography (SiO$_2$, eluant 1: EtOAc, eluant 2: EtOAc/EtOH=4/1, Rf of the product 0.36, Rf of Ph$_3$PO 0.71 in EtOAc: EtOH=5:1).

A solid (6.59 g, yield 76%) with a melting point of 130° C. was obtained.

The molar purity was greater than 88% ($^1$H NMR).

The 3-methoxy-4-[2-(2-oxoimidazolidin-1-yl)ethoxy]benzaldehyde obtained was directly used in the next step without further purification.

$^1$H and $^{13}$C NMR Characterization

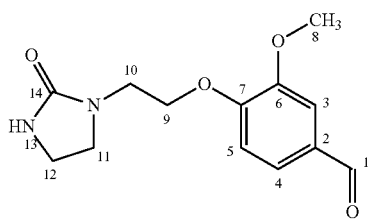 [SMILES: COc1cc(C=O)ccc1OCCN1CCNC1=O]

TABLE 8

| No. atoms | δ of $^1$H (ppm) | δ of $^{13}$C (ppm) |
|---|---|---|
| 1 | 9.78 | 191.1 |
| 2 | / | 129.6 |
| 3 | 7.34 | 109.6 |
| 4 | 7.48 | 125.6 |
| 5 | 7.14 | 112.0 |
| 6 | / | 148.9 |
| 7 | / | 152.9 |
| 8 | 3.78 | 55.4 |
| 9 | 4.11 | 67.3 |
| 10 | 3.42 | 45.5 |
| 11 | 3.38 | 42.3 |
| 12 | 3.16 | 37.2 |
| 13 | 6.33 | / |
| 14 | / | 161.9 |

Solvent used: DMSO—Calibration on the signal of DMSO at 2.44 ppm in $^1$H, 39.5 ppm in $^{13}$C.

b) Preparation of 3-methoxy-4-[2-(2-oxoimidazolidin-1-yl)ethoxy]benzaldehyde oxime

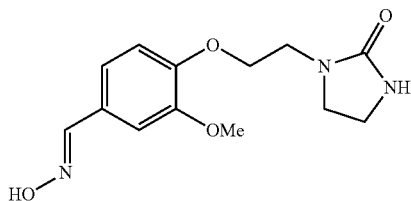 [SMILES: COc1cc(/C=N/O)ccc1OCCN1CCNC1=O]

A solution of hydroxylamine (10.2 g, 0.155 mol, 50% in water, Aldrich) in EtOH (20 ml) was added to a solution of 3-methoxy-4-[2-(2-oxoimidazolidin-1-yl)ethoxy]benzaldehyde (25.6 g, 0.097 mol) in EtOH (250 ml) at 52° C. The reaction medium was then stirred for 4.5 hours at between 50 and 60° C. The reaction medium was then concentrated under reduced pressure ($T_{bath}$=42° C., 60 mbar) so as to obtain a residue of 70-80 ml. The precipitate obtained was filtered off, washed with an EtOH/water mixture (twice 5 ml/15 ml) and dried under atmospheric pressure at ambient temperature.

A white solid (22.14 g, yield 82%) with a melting point of 189° C. was obtained.

The molar purity was greater than 89% ($^1$H NMR).

$^1$H and $^{13}$C NMR Characterization

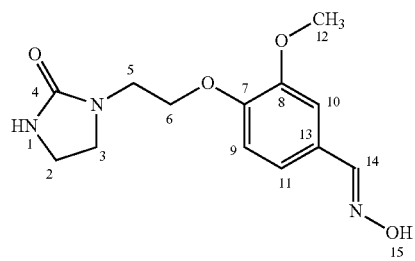 [SMILES: COc1cc(/C=N/O)ccc1OCCN1CCNC1=O]

TABLE 9

| No. atoms | δ of $^1$H (ppm) | δ of $^{13}$C (ppm) |
|---|---|---|
| 1 | 6.30 | / |
| 2 | 3.16 | 37.1 |
| 3 | 3.35 | 42.4 |
| 4 | / | 161.9 |
| 5 | 3.42 | 45.4 |
| 6 | 4.00 | 67.0 |
| 7 | / | 148.5 |
| 8 | / | 148.9 |
| 9 | 6.93 | 112.8 |
| 10 | 7.15 | 108.6 |
| 11 | 7.01 | 119.9 |
| 12 | 3.72 | 55.2 |
| 13 | / | 125.9 |
| 14 | 7.98 | 147.5 |
| 15 | 10.92 | / |

Solvent used: DMSO—Calibration on the signal of DMSO at 2.44 ppm in $^1$H, 39.5 ppm in $^{13}$C.

c) Preparation of 3-methoxy-4-[2-(2-oxoimidazolidin-1-yl)ethoxy]benzonitrile oxide

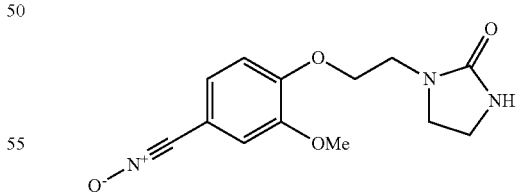

An aqueous solution of NaOCl in water (Aldrich, >4% of active chloride) (161 ml) was added dropwise, over a period of 10 minutes, to a suspension of 3-methoxy-4-[2-(2-oxoimidazolidin-1-yl)ethoxy]benzaldehyde oxime (21.7 g, 0.078 mol) in CH$_2$Cl$_2$ (950 ml) at −3° C. The reaction medium was then stirred for 20 minutes at 0° C. The organic phase was separated and the aqueous phase was extracted with CH$_2$Cl$_2$ (4 times with 100 ml). The combined organic phases were washed with water (3 times with 100 ml), dried over Na$_2$SO$_4$, and then concentrated under reduced pressure ($T_{bath}$ 22° C.) to 200-220 ml. The precipitate obtained was filtered off, washed with $CH_2Cl_2$ (twice with 10 ml) and dried under atmospheric pressure at ambient temperature.

A solid (9.13 g, yield 42%) with a melting point of 109-111° C. with decomposition was obtained.

The molar purity was greater than 80% ($^1$H NMR). With recrystallization from EtOH, the purity of the compound was greater than 90% by mass.

$^1$H and $^{13}$C NMR Characterization

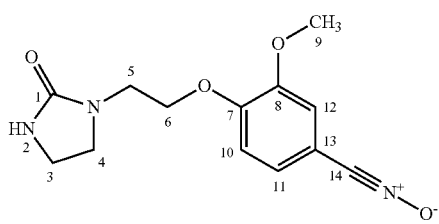 [SMILES: COc1cc(C#[N+][O-])ccc1OCCN1CCNC1=O]

TABLE 10

| No. atoms | δ of $^1$H (ppm) | δ of $^{13}$C (ppm) |
|---|---|---|
| 1 | / | 163.5 |
| 2 | 6.31 | / |
| 3 | 3.15 | 37.2 |
| 4 | 3.35 | 42.3 |
| 5 | 3.40 | 45.4 |
| 6 | 4.04 | 67.1 |
| 7 | / | 150.4 |
| 8 | / | 148.4 |
| 9 | 3.73 | 55.6 |
| 10 | 7.03 | 113.0 |
| 11 | 7.25 | 125.8 |
| 12 | 7.32 | 115.2 |
| 13 | / | 106.2 |
| 14 | / | Not visible |

Solvent used: DMSO—Calibration on the signal of DMSO at 2.44 ppm in $^1$H, 39.5 ppm in $^{13}$C.

Infrared Characterization (KBr Pellet)
ν ($cm^{-1}$): 2305 (function Ar—C≡N→O)

Mass Spectrometry Characterization
$C_{13}H_{15}N_3O_4$, Mw=277.27 g/mol

The samples were analyzed by direct introduction into the mass spectrometer, using the electrospray ionization mode (DI/ESI).

Preparation of the Sample
Approximately 20 mg of sample were placed in solution in 25 ml of methanol, then diluted to 1/100 for the DI/ESI analysis.

Positive Mode:
m/z: 300 ([[M+Na]$^+$), 577 ([2M+Na]$^+$)

Example 4

Preparation of (Z,E)-N-(4-(2-(2-oxoimidazolidin-1-yl)ethylcarbamoyl)benzylidene)aniline oxide This compound can be prepared from 4-formylbenzoic acid and 2-aminoethylimidazolidone according to the following synthesis scheme:

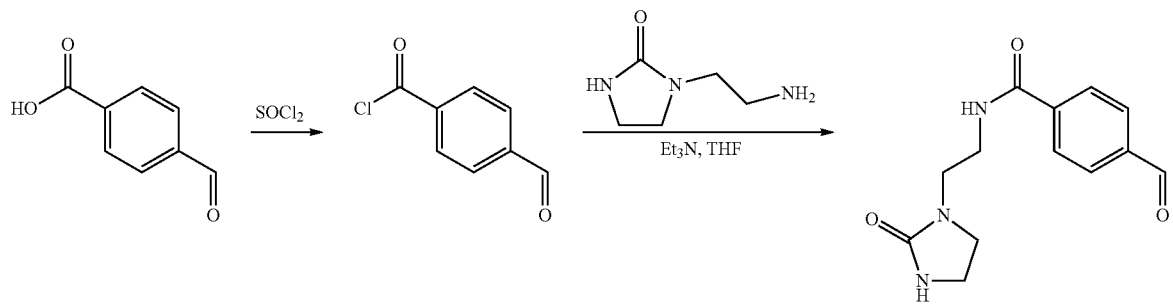

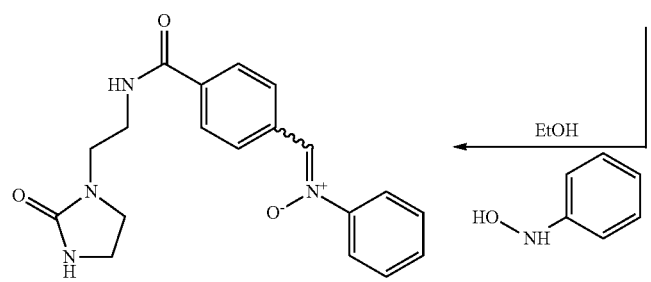

a) Preparation of 4-formylbenzoyl chloride

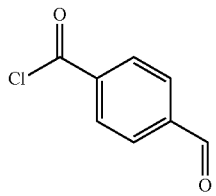 [SMILES: O=Cc1ccc(C(=O)Cl)cc1]

The synthesis of this compound is described in the following references: JANSSEN PHARMACEUTICA N.V.; WO2007/53386; (2007); (A2). The melting point of the 4-formylbenzoyl chloride synthesized is in accordance with the data described in the following references: Graffner-Nordberg, Malin; Sjoedin, Karin; Tunek, Anders; *Hallberg, Anders Chemical & Pharmaceutical Bulletin*, 1998 vol. 46, 4, p. 591-601 and Kuhlmann; *Alexander Inorganica Chimica Acta*, 1979, vol. 34, p. 197,207 and *Simonis Chemische Berichte*, 1912, vol. 45, p. 1586.

b) Preparation of 4-formyl-N-[2-(2-oxoimidazolidin-1-yl)ethyl]benzamide

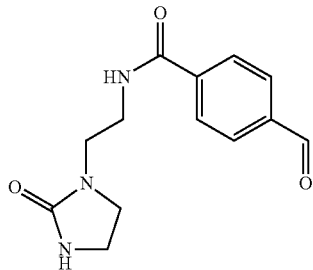 [SMILES: O=Cc1ccc(C(=O)NCCN2CCNC2=O)cc1]

A solution of the 4-formylbenzoyl chloride (16.5 g, 0.098 mol) in dry THF (100 ml) was added, over a period of minutes, to a suspension of 1-(2-amino-ethyl)imidazolidin-2-one (12.6 g, 0.098 mol) and Et$_3$N (19.8 g, 0.195 mol) in dry THF (300 ml) at −35° C. During the addition, the temperature of the reaction medium was maintained between −35 and −38° C. The temperature of the reaction medium was then slowly brought back to ambient temperature over a period of 4 hours. The precipitate obtained (mainly the expected product as a mixture with triethylamine hydrochloride Et$_3$N.HCl) was filtered off and washed with THF (twice with 20 ml). The reaction crude was solubilized in an aqueous solution of Na$_2$CO$_3$ (3.4 g, 0.032 mol in 40 ml of water). The expected compound was extracted several times with EtOAc (total volume: 3.5 l).

The combined organic phases were dried over Na$_2$SO$_4$ and concentrated under reduced pressure (T$_{bath}$=40° C.)

A solid (5.53 g, yield 22%) with a melting point of 138° C. was obtained.

The molar purity was greater than 81% ($^1$H NMR). This compound was directly used in the next step without further purification.

$^1$H and $^{13}$C NMR Characterization

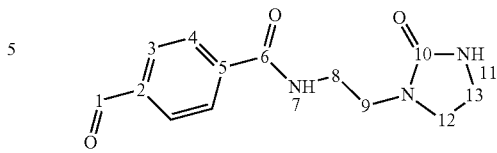

TABLE 11

| No. atoms | δ of $^1$H (ppm) | δ of $^{13}$C (ppm) |
|---|---|---|
| 1 | 10.01 | 192.6 |
| 2 | / | 137.4 |
| 3/4 | 7.93 | 128.2 + 129.7 |
| 5 | / | 139.3 |
| 6 | / | 165.2 |
| 7 | 8.69 | / |
| 8 | 3.33 | 38.2 |
| 9 | 3.18 | 42.9 |
| 10 | / | 162.0 |
| 11 | 6.24 | / |
| 12 | 3.35 | 45.0 |
| 13 | 3.15 | 37.9 |

Solvent used: DMSO—Calibration on the signal of DMSO at 2.44 ppm in $^1$H, 39.5 ppm in $^{13}$C.

c) Preparation of N-phenylhydroxylamine

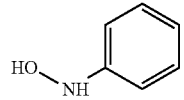

The synthesis of this compound from nitrobenzene is described in *Organic Syntheses*, Coll. Vol. 1. p. 445 (1941); Vol. 4. p. 57 (1925).

d) Preparation of (Z,E)-N-(4-(2-(2-oxoimidazolidin-1-yl)ethylcarbamoyl)benzylidene)aniline oxide

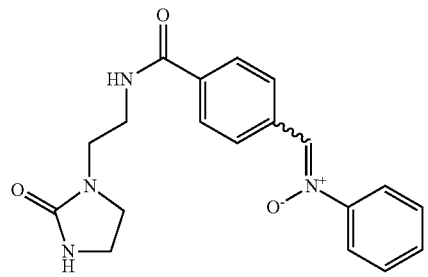 [SMILES: O=C(NCCN1CCNC1=O)c1ccc(C=[N+]([O-])c2ccccc2)cc1]

A solution of N-phenylhydroxylamine (2.21 g, 0.020 mol) in EtOH (10 ml) was added to a solution of 4-formyl-N-[2-(2-oxoimidazolidin-1-yl)ethyl]benzamide (5.3 g, 0.020 mol) in EtOH (50 ml). The reaction mixture was brought to reflux for 4 hours and then cooled to ambient temperature. The precipitate obtained was filtered off, washed with EtOH (3 times with 5 ml) and air-dried at ambient temperature.

A white solid (4.65 g, yield 66%) with a melting point of 209° C. was obtained.

The molar purity was greater than 92% ($^1$H NMR).
$^1$H and $^{13}$C NMR Characterization

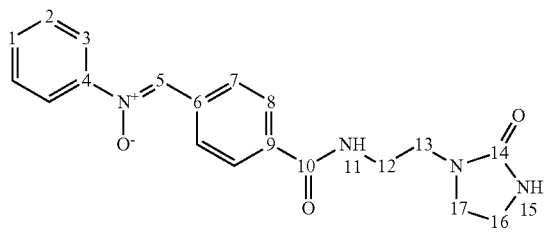

TABLE 12

| No. atoms | δ of $^1$H (ppm) | δ of $^{13}$C (ppm) |
|---|---|---|
| 1/2 | 7.50 | 128.9 + 129.9 |
| 3 | 7.87 | 121.3 |
| 4 | / | 148.1 |
| 5 | 8.53 | 132.7 |
| 6 | / | 133 |
| 7 | 8.47 | 128.2 |
| 8 | 7.87 | 126.9 |
| 9 | / | 135.3 |
| 10 | / | 165.3 |
| 11 | 8.58 | / |
| 12 | 3.33 | 37.5 |
| 13 | 3.18 | 42.4 |
| 14 | / | 162.1 |
| 15 | 6.25 | / |
| 16 | 3.16 | 37.2 |
| 17 | 3.36 | 44.5 |

Solvent used: DMSO—Calibration on the signal of DMSO at 2.44 ppm in $^1$H, 39.5 ppm in $^{13}$C.

Mass Spectrometry Characterization
$C_{19}H_{20}N_4O_3$, Mw=352.38 g/mol

The sample was analyzed by direct introduction into the mass spectrometer, using electrospray as ionization mode (DI/ESI).

Preparation of the Sample:
Approximately 20 mg of sample were placed in solution in 0.5 ml of DMSO+24.5 ml of methanol, then diluted to 1/100 in methanol for the DI/ESI analysis.

Positive Mode
m/z: 375 ([M+Na]$^+$), 727 ([2M+Na]$^+$)
Negative Mode
m/z: 351 ([M=H]$^-$), 703 ([2M-H]$^-$)

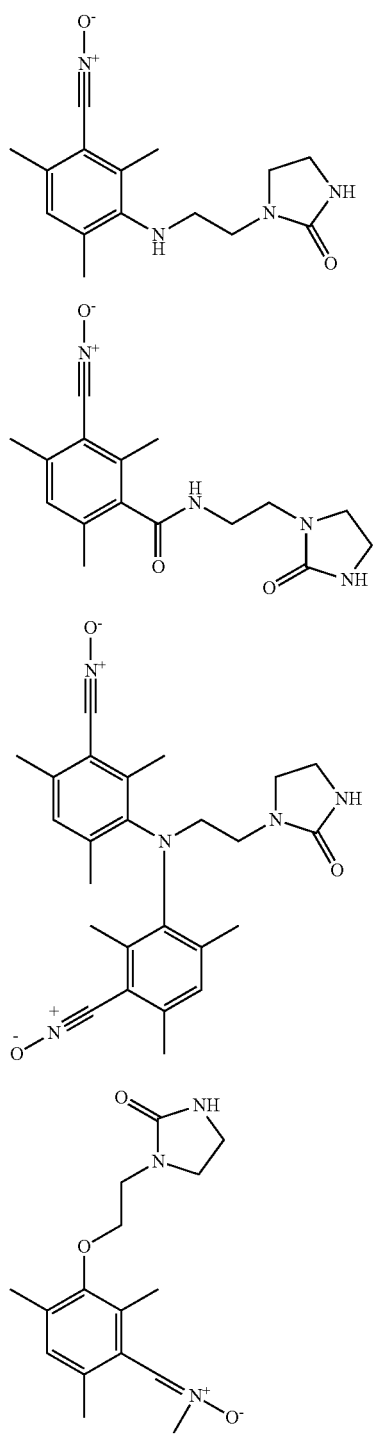
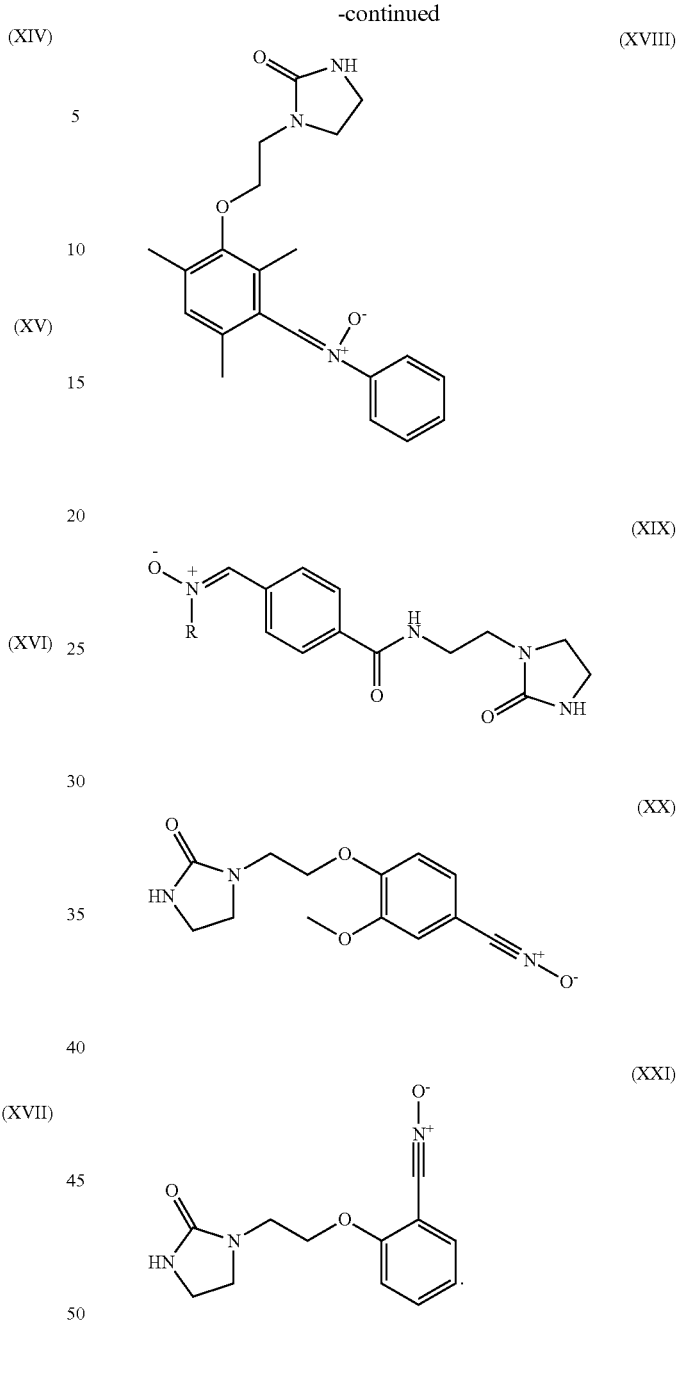

The invention claimed is:

1. A compound comprising at least one group Q and at least one group A linked together by at least one spacer group Sp, wherein:
   Sp is an atom or a group of atoms forming a link between group Q and group A;
   the group Q is a group of formula (XI):

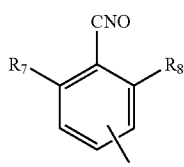

(XI)

wherein R7 and R8 independently represent a $C_1$-$C_5$ alkyl group or a halogen; and
the group A is a group of formula (XII):

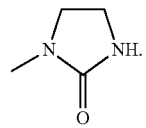

(XII)

2. The compound of claim 1, wherein the spacer group Sp is a linear or branched $C_1$-$C_{24}$ alkyl chain, optionally comprising one or more nitrogen or oxygen atoms.

3. The compound of claim 1, wherein the spacer group Sp is a linear or branched $C_1$-$C_{10}$ alkyl chain, optionally comprising one or more nitrogen or oxygen atoms.

4. The compound of claim 1, wherein the spacer group Sp is a linear $C_1$-$C_6$ alkyl chain, optionally comprising one or more nitrogen or oxygen atoms.

5. A compound comprising at least one group Q and at least one group A linked together by at least one spacer group Sp, wherein:
   Sp is an atom or a group of atoms forming a link between group Q and group A;
   the group Q is a group of formula (XI):

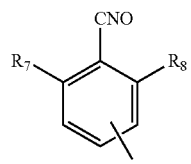

(XI)

wherein R7 and R8 independently represent a methyl group or a chlorine atom; and
the group A is a group of formula (XII)

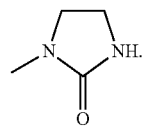

(XII)

6. A compound, wherein the compound is chosen from compounds of formulae (XIII) to (XXI):

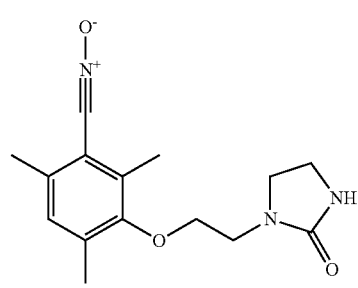

(XIII)